United States Patent
Hasegawa et al.

(10) Patent No.: US 6,404,846 B1
(45) Date of Patent: Jun. 11, 2002

(54) FLUORESCENT X-RAY METHOD FOR DETERMINING X-RAY ALIGNMENT BY LUMINESCENT CHANGES

(75) Inventors: Kiyoshi Hasegawa; Yuuya Sone, both of Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/531,662

(22) Filed: Mar. 20, 2000

(30) Foreign Application Priority Data

Mar. 18, 1999 (JP) .......................................... 11-073853

(51) Int. Cl.[7] .......................................... G01N 23/223
(52) U.S. Cl. .............................. 378/44; 378/62; 378/63; 378/206
(58) Field of Search .................. 378/49, 204, 205, 378/206, 207, 44, 45, 46, 62, 63; 250/208, 559.07, 559.08, 559.29, 559.3

(56) References Cited

U.S. PATENT DOCUMENTS

| | | | |
|---|---|---|---|
| 5,978,091 A | * | 11/1999 | Jann et al. ................... 356/376 |
| 6,115,450 A | * | 9/2000 | Jasegawa ..................... 378/50 |
| 6,155,450 A | * | 9/2000 | Hasegawa ..................... 378/50 |

* cited by examiner

Primary Examiner—Robert H. Kim
Assistant Examiner—Hoon K. Song
(74) Attorney, Agent, or Firm—Adams & Wilks

(57) ABSTRACT

A fluorescent X-ray analysis method comprises examining a positional relationship between an image of a sample and an X-ray illuminated region of the sample image, acquiring an image of the sample as a monochromatic image, extracting from the acquired sample image a coincident portion thereof containing the X-ray illuminated region, and examining a luminance change in the extracted image and, where there is a luminance change greater than a reference value, determining whether or not the X-ray illuminated to the sample is partly off the sample.

8 Claims, 9 Drawing Sheets

FIG. 6
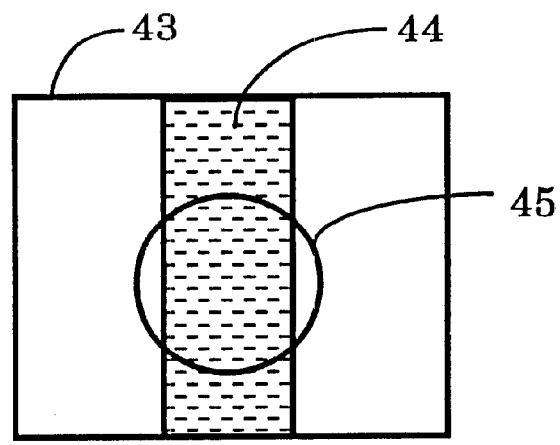
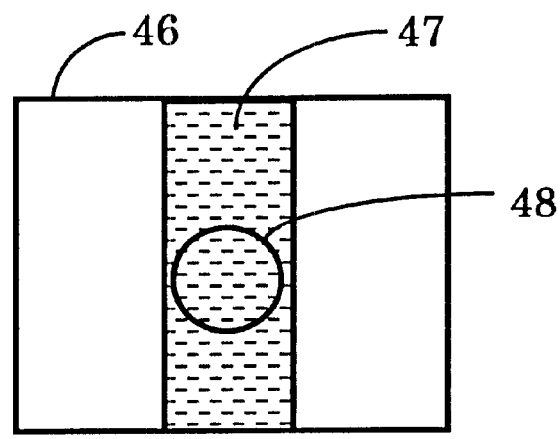
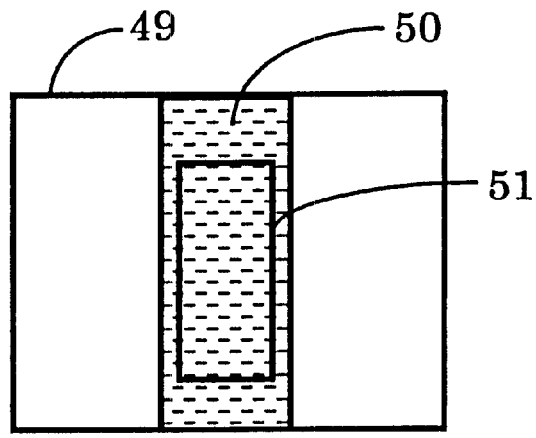

FIG. 7
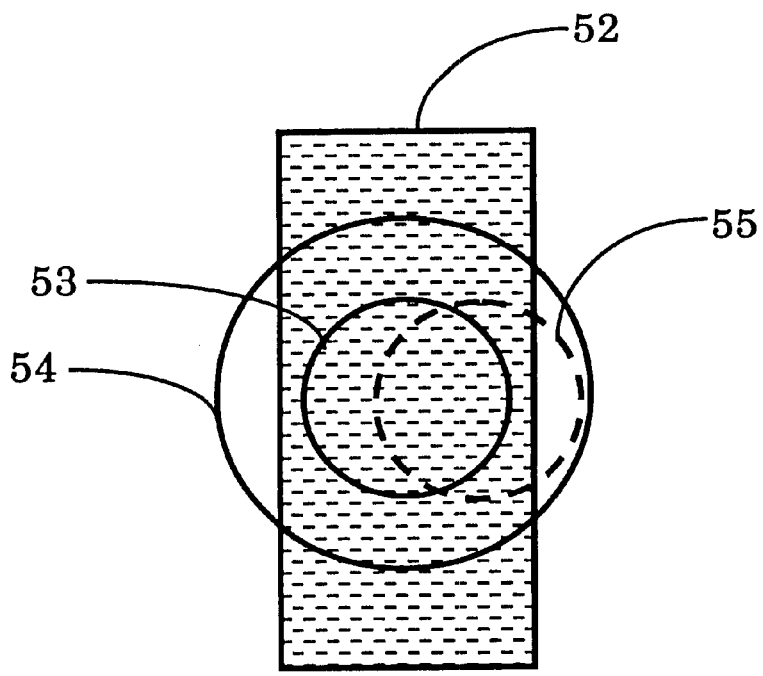
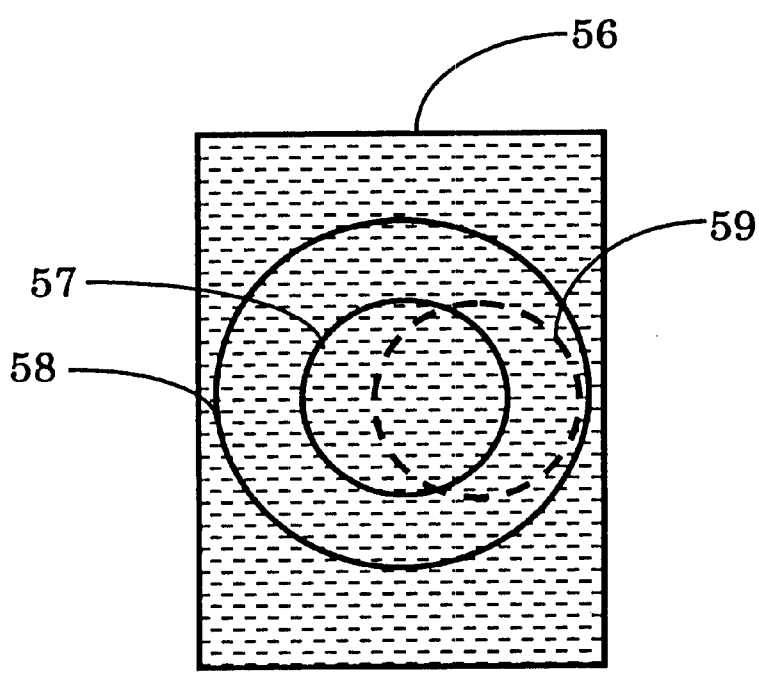

FIG. 8
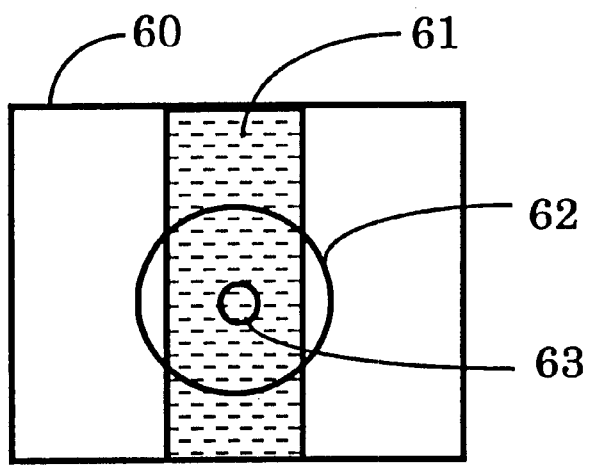
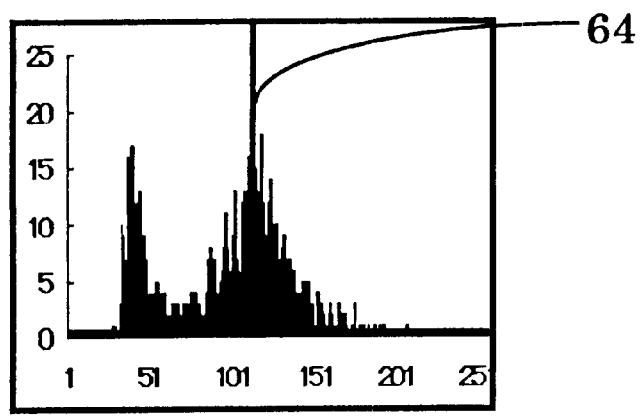
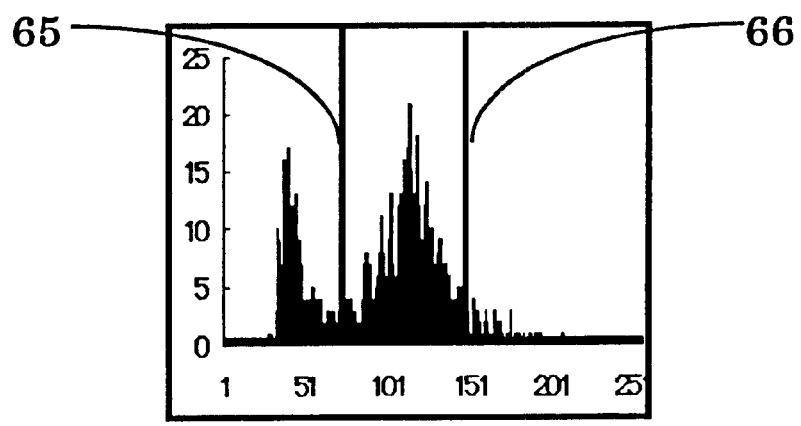

FLUORESCENT X-RAY METHOD FOR DETERMINING X-RAY ALIGNMENT BY LUMINESCENT CHANGES

BACKGROUND OF THE INVENTION

This invention relates to an analysis apparatus utilizing a fluorescent X-ray.

In an apparatus utilizing a fluorescent X-ray, if an X-ray illuminated to a sample partly goes off the sample, variation occurs in the fluorescent X-ray intensity obtained. In the case of conducting a quantitative analysis utilizing a magnitude in fluorescent X-ray intensity, in almost all cases the analysis value is an erroneous value.

FIG. 3 shows a conventional fluorescent X-ray analysis apparatus having an X-ray generating part 14 for illuminating an X-ray to a sample 20 disposed on a sample stage 19, a collimator 15 for collimating the X-ray illuminated to the sample 20, and an X-ray detecting part 16 for detecting a fluorescent X-ray generated from the sample 20. An imaging section 18 obtains a sample image of the X-ray illuminated to the sample 20 via a mirror 17. An image monitor section 21 receives the sample image from the imaging section 18. Utilizing a size-confirming division displayed on the image monitor section 21, it is possible to visually confirm whether the X-ray illuminated to the sample 20 is off the sample or not. Another conventional apparatus displays a region to be illuminated by the X-ray on the image monitor section 21. However, in this case confirmation of whether the X-ray illuminated to the sample 20 is off the sample or not is also made visually by a human who is operating the apparatus.

However, these apparatuses have a defect that no confirmation is possible whether the X-ray illuminated to a sample is not off the sample unless confirmation operation is made by a human. The recent analysis/measurement apparatus has reached the state that automation is necessary from the viewpoint of reducing personnel expenses and removing human error. A first problem is to automatically determine that the X-ray illuminated to a sample is not extended out of the sample.

The analysis apparatuses includes an apparatus provided with a plurality of collimators to restrict an X-ray. Where conducting a sample measurement, a collimator is selected matched to a shape or size of a sample by a human. A second problem is to automate this operation.

A third problem is, where determination is difficult by a monochromatic image, to extract a particular color and perform a determination process.

Where an analysis apparatus has being used for a long term or where environmental change such as temperature is severe, there is a fear that a center position in X-ray illumination deviates or X-ray illumination dimension changes. Due to this, when determining whether the X-ray illuminated to a sample is off or not, an X-ray illumination region is assumed a little greater than an actual size, whereby it is possible to cope with deviation in X-ray center axis and change in X-ray illumination range. Consequently, a fourth problem is to give margins to an X-ray illumination region individually in vertical direction and horizontal direction and solving the problem of X-ray extending out.

A fifth problem is to detect by what means whether an X-ray illuminated to a sample is extended out.

There is a situation that a smaller sample is to be measured than an X-ray illumination region. Accordingly, a sixth problem is to enable sample quantitative analysis even where determining that an X-ray illuminated to the sample is partly off the sample.

SUMMARY OF THE INVENTION

The present invention adopted the following means in order to solve the problems.

In a fine-part fluorescent X-ray apparatus having an X-ray generating part for illuminating an X-ray to a sample, an X-ray detecting part for detecting a fluorescent X-ray from the sample; a collimator part for restricting the X-ray illuminated to the sample, an imaging part for imaging a sample image, and an image processing part for image-processing an image imaged, as a former process a positional relationship is previously examined between a sample image to be acquired in the imaging part and an illumination region of an X-ray.

As process procedure 1 is acquired an image of the sample in a monochromatic image.

As process procedure 2 is extracted, in the acquired image of the sample, a coincident portion of the image with the X-ray illumination region by image processing means.

As process procedure 3 is examined a luminance change in the extracted image and, where there is a luminance change greater than a reference, determination is made that the X-ray illuminated to the sample is partly off the sample.

The apparatus is provided with a plurality of collimators to restrict the X-ray illuminated to the sample, repeatedly executes the determination process by the number of the collimators, and selects a collimator greatest in area among collimators that the X-ray is not off.

The image acquiring operation conducted in the process procedure 1 acquires the image of the sample in a color image, has means to extract a particular color from the acquired image and convert same into a monochromatic image, and can determine utilizing color information whether the X-ray illuminated to the sample is partly off the sample or not. A fluorescent X-ray analysis apparatus is thus structured.

The operation of extracting by an image processing means a coincident portion of an image with the X-ray illumination region conducted in the process procedure 2 can magnify information of the X-ray illumination region at arbitrary magnifications independently in vertical direction and horizontal direction to determine whether the X-ray illuminated to the sample is partly off the sample or not thereby giving a margin for axis deviation of X-ray illumination and change in illumination region.

As a first method of the process procedure 3, luminance change examination, a frequency distribution of luminance in the extracted image is calculated, a smoothing processing is made on frequency distribution data, the number of peaks concerning luminance is examined from a frequency distribution after smoothing.

It can be determined that the X-ray illuminated to the sample is partly off the sample where two or more peaks are found.

As a second method of the process procedure 3, luminance change examination, in the extracted image binarization is made with a designated threshold, and measurement is made on an area of pixels of a designated value of 1 or 0 after binarization.

It can be determined that the X-ray illuminated to the sample is partly off the sample where there is a significant difference between an area of an X-ray illumination range and an area measured.

As a third method of the process procedure 3, luminance change examination, an image luminance in the vicinity of the center of the X-ray illumination region is rendered as a reference luminance, measurement is made in the extracted image an area of pixels close to the reference luminance, and it can be determined whether the X-ray illuminated to the sample is partly off the sample or not, where there is a significant difference between an area of an X-ray illumination range and an area measured.

In the second and third methods of luminance change examination, it is determined whether the X-ray illuminated to the sample is partly off the sample or not, an area of a sample portion obtained by measurement is rendered as a sample area, the sample area is divided by the area of the X-ray illumination region to calculates a real illumination area ratio, an X-ray is illuminated to the sample in this state, a fluorescent X-ray intensity obtained in the X-ray detection part is divided by the real illumination area ratio thereby enabling estimation of a fluorescent X-ray intensity where the sample exists in the entire X-ray illumination region, and an estimated fluorescent X-ray intensity can be utilized for quantitative analysis.

BRIEF DESCRIPTION OF THE DRAWINGS

FIG. 6 is a figure showing a relationship between a collimator different in X-ray illumination region and a sample.

FIG. 7 is a figure showing to determine whether an X-ray illuminated to a sample is partly off the sample or not, by giving a margin to the X-ray illumination region.

FIG. 8 is an explanatory view when automatically generating a condition for making binary an image.

Figure 1:
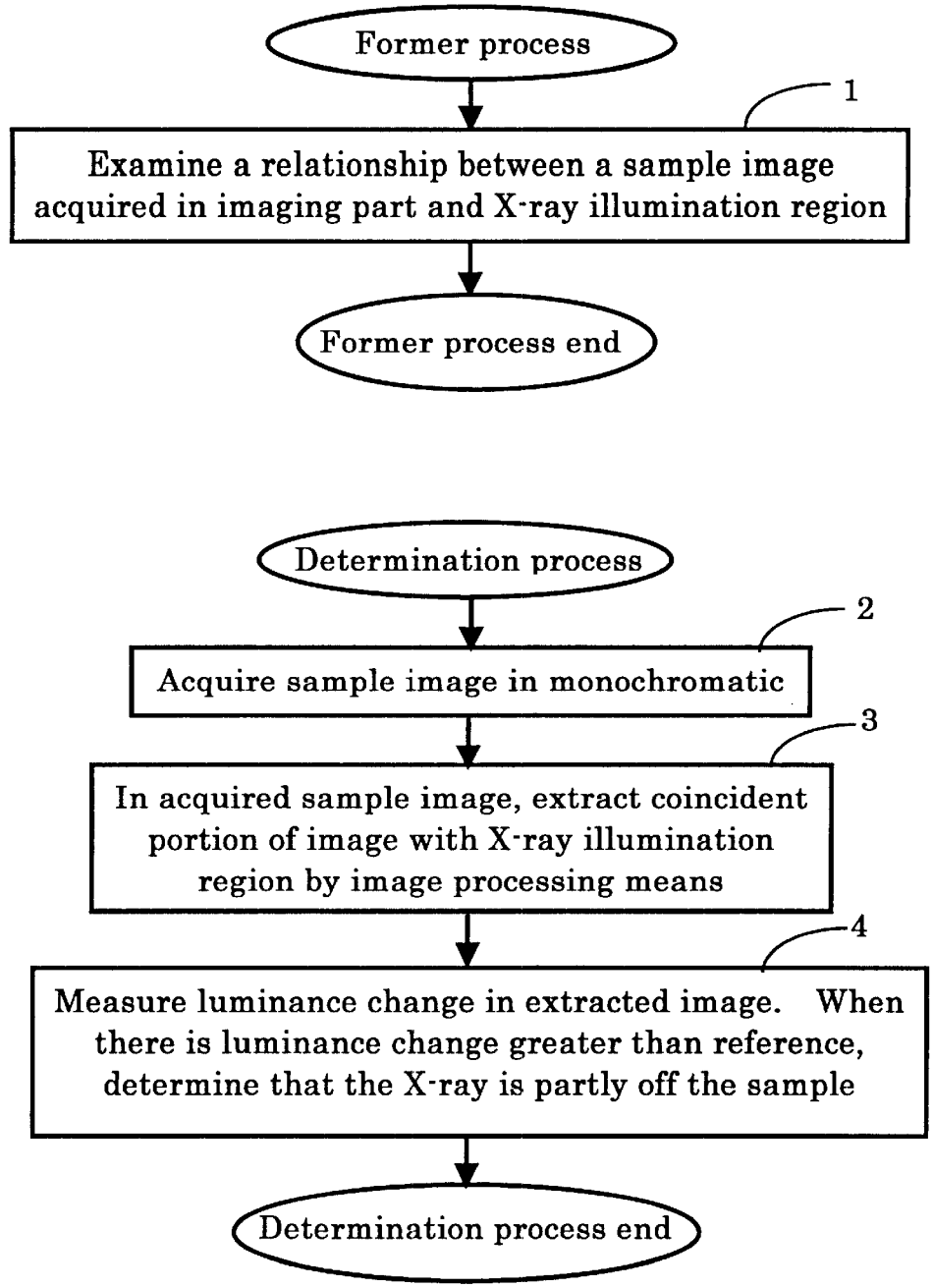
FIG. 1 is a flowchart of a procedure to determine whether an X-ray illuminated to a sample is partly off the sample or not.

Explanation of the Reference Numerals and Symbols

1 . . . Former process content
2 . . . determination process first procedure
3 . . . determination process second procedure
4 . . . determination process third procedure
5 . . . X-ray generating part
6 . . . X-ray collimator
7 . . . Fluorescent X-ray detecting part
8 . . . Mirror for acquiring a sample image
9 . . . Sample image imaging part
10 . . . Sample stage
11 . . . Sample
12 . . . Image processing part
13 . . . Determination result display part
14 . . . X-ray generating part
15 . . . X-ray collimator
16 . . . Fluorescent X-ray detecting part
17 . . . Mirror for acquiring a sample image
18 . . . Sample image imaging part
19 . . . Sample stage
20 . . . Sample
21 . . . Sample image monitor part
22 . . . Procedure 1 of a method utilizing frequency distribution
23 . . . Procedure 2 of a method utilizing frequency distribution
24 . . . Procedure 3 of a method utilizing frequency distribution
25 . . . Procedure 4 of a method utilizing frequency distribution
26 . . . Procedure 5 of a method utilizing frequency distribution
27 . . . Imaged sample
28 . . . Sample
29 . . . Line for explaining an X-ray illumination region
30 . . . Image of a coincident portion with the X-ray illumination region
31 . . . Luminance frequency distribution
32 . . . Luminance frequency distribution after smoothing
33 . . . Procedure 1 of a method utilizing a binary process
34 . . . Procedure 2 of a method utilizing a binary process
35 . . . Procedure 3 of a method utilizing a binary process
36 . . . Procedure 4 of a method utilizing a binary process
37 . . . Procedure 5 of a method utilizing a binary process
38 . . . Imaged image
39 . . . Sample
40 . . . Line for explaining an X-ray illumination region
41 . . . Image of a coincident portion with the X-ray illumination region
42 . . . Image after binary process
43 . . . Imaged image
44 . . . Sample
45 . . . X-ray illumination region
46 . . . Imaged image
47 . . . Sample
48 . . . X-ray illumination region
49 . . . Imaged image
50 . . . Sample
51 . . . X-ray illumination region
52 . . . Sample
53 . . . X-ray illumination region displayed by the apparatus
54 . . . X-ray illumination region given vertically and horizontally a margin
55 . . . X-ray illumination region when deviated in illumination position
56 . . . Sample
57 . . . X-ray illumination region displayed by the apparatus
58 . . . X-ray illumination region given vertically and horizontally a margin
59 . . . X-ray illumination region when deviated in illumination position
60 . . . Imaged image
61 . . . Sample
62 . . . X-ray illumination region
63 . . . Image at around a center of X-ray illumination
64 . . . Mean luminance at around a center of X-ray illumination
65 . . . Lower limit value of binarizing
66 . . . Upper limit value of binarizing
67 . . . Sample stage
68 . . . Wire rod
69 . . . X-ray illumination region

DETAILED DESCRIPTION OF THE PREFERRED EMBODIMENTS

Hereunder, embodiments of the invention will be described with reference to the drawings.

Figure 2:
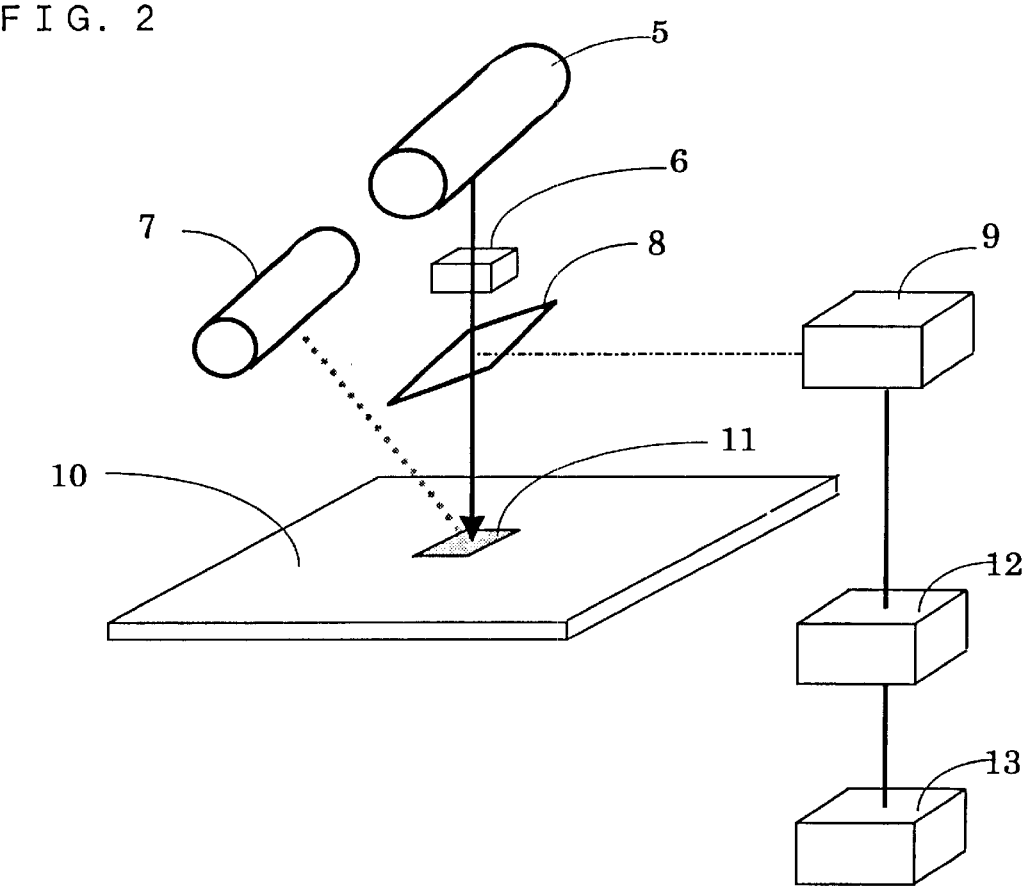
FIG. 2 is a figure showing a structural example of an apparatus for realizing the present invention.
Figure 3:
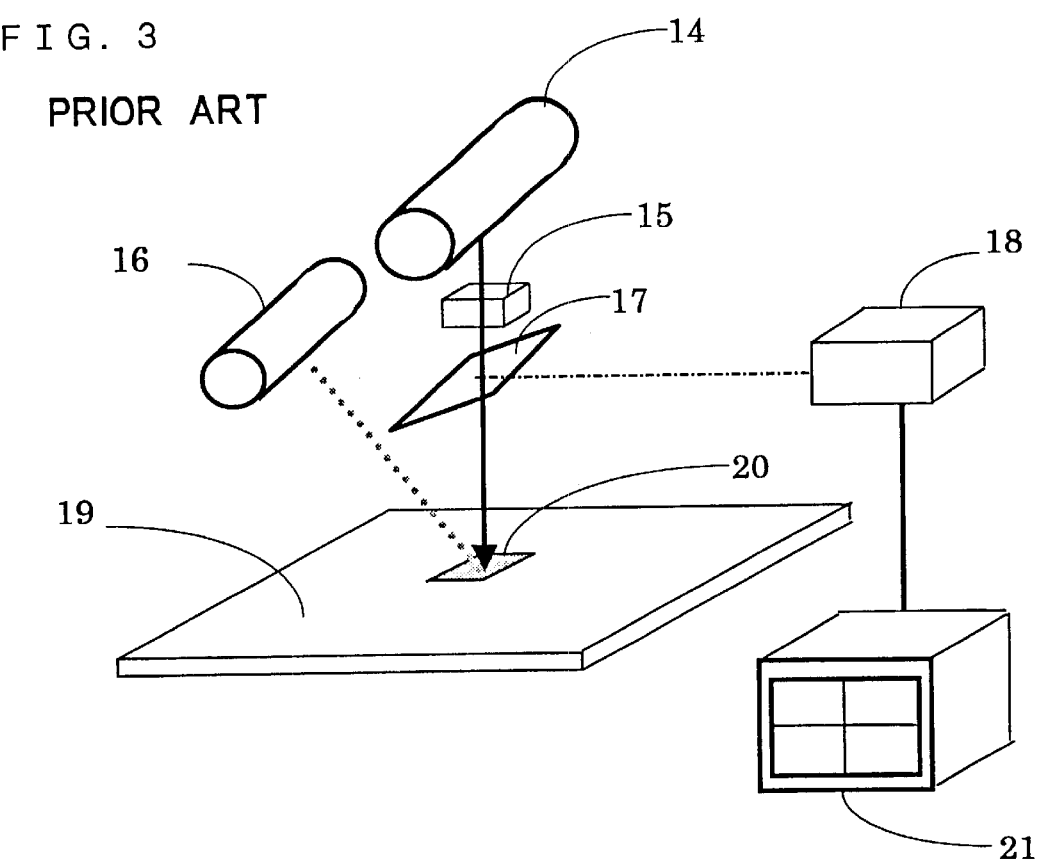
FIG. 3 is a figure showing a structural example of a conventional apparatus.

FIG. 2 shows a fluorescent X-ray analysis apparatus according to the present invention. The fluorescent X-ray analysis apparatus has an X-ray generating part 5 for illuminating an X-ray to a sample 11 disposed on a sample stage 10, a collimator 6 for collimating the X-ray illuminated to the sample 11, an X-ray detecting part 7 for detecting a fluorescent X-ray generated from the sample 11, an imaging section 9 for obtaining a sample image of the X-ray illuminated to the sample 11 via a mirror 8, an image processing section 12 such as a computer or processor for image-processing the sample image to determine whether the X-ray illuminated to the sample is partly off the sample, and a display section 13 for displaying the determination results. The imaging section 9 comprises, for example, a monochromatic CCD camera. An image signal outputted from the CCD is received by the image processing section 12–13 and stored.

A process for confirming whether the X-ray illuminated to the sample 11 is partly off the sample using the fluorescent X-ray analysis apparatus according to the present invention is described below.

Referring now to FIG. 1, as a procedure of a former process (block 1), in order to examine the relationship between an X-ray illumination region and the sample 11, measurement is made on the position, shape and dimension of the X-ray illumination region in an image obtained by the imaging section 9. As an example of center coordinate measurement, the position of the X-ray illumination region uses a center coordinate of the X-ray illumination region.

A fluorescent X-ray is then obtained. Metals A and B different in material are bonded together in a manner forming a linear boundary to form a sample. An X-ray is illuminated in a state that the entire X-ray illumination region is illuminated to the metal A, and a fluorescent X-ray intensity obtained in a fluorscent X-ray energy region of the metal A is rendered as A.

Next, an X-ray is illuminated in a state that the entire X-ray illumination region is illuminated to the metal B, and an X-ray intensity obtained in a fluorescent X-ray energy region of the metal A is rendered as B.

In an XY plane, the linear metal boundary is brought into parallel with a Y axis. While moving the sample in an X direction, a position is searched for that an X-ray intensity obtained in a fluorescent X-ray energy region of metal A becomes a mean value of the intensity A and intensity B. The sample is imaged in a found state. A metal boundary on the image is taken as a center x coordinate of an X-ray illumination region.

Similarly, the linear metal boundary is brought into parallel with an X axis. While moving the sample in the Y direction, a position is searched for that an X-ray intensity obtained in a fluorescent X-ray energy region of metal A becomes a mean value of the intensity A and intensity B. The sample is imaged in a found state. A metal boundary on the image is taken as a center Y coordinate of the X-ray illumination region.

With the above operation, it is possible to obtain a center coordinate of an X-ray illumination region on an image.

As an example of measuring a shape and dimension of an X-ray illumination region, a shape and dimension of X-ray illumination is measured using a photo-sensitive film and converted into a shape and dimension on an image.

Also, in the case of such a small X-ray illumination region that measurement can not be made with the photo-sensitive film, a dimension is measured by utilizing the X-ray beam width measurement method disclosed in Japanese Patent Laid-open No. 300853/1994 and converted into a dimension on an image.

In the above, measurement can be made on a position, shape and dimension of an X-ray illumination region in an image obtained by the imaging section in order to grasp a relationship between the X-ray illumination region and the sample.

Next, an explanation is given of a procedure to determine whether the X-ray illuminated to the sample is partly off the sample or not.

First, as a procedure 1 of a determination process of FIG. 1, an image of a sample to be measured is obtained (block 2). As imaging means, a monochromatic CCD camera for example is used. An image signal outputted from the CCD camera is received by an image processing section to store the sample image in the image processing section. As a means for storing image data, if for example the horizontal resolution is horizontally 640 pixels and vertically 480 pixels and the resolution concerning luminance is 256 steps, realization is by preparing a two-dimensional data area with 640×480 and 8 bits and storing luminance information of each pixel.

Second, as procedure 2 of the determination process of FIG. 1, in the sample image obtained, a coincident portion of the image with the X-ray-illumination region is extracted by the image processing means (block 3).

As an example of an extraction means, explanation is made on a case that-the number of obtained image pixels is 640×480, the luminance resolution on each pixel is 256 stages and the X-ray illumination region is in a oval form.

A two-dimensional data area is prepared to store data having a size of 640×480 and luminance information of 256 stages, and all the data is rendered 0.

In order to set a flag for the coincident portion with the X-ray illumination region in the two-dimensional data area, 1 is set to a relevant portion by utilizing the position, shape and dimension of the X-ray illumination region. In this example, because 1 is set to a relevant portion, realization is made by drawing an oval and rendering a set value as 1 with utilizing the image processing means.

Multiplication is made between the obtained sample image and the two-dimensional data area. The result of multiplication is stored in the two-dimensional data area. By the above procedure, a coincident image with the X-ray illumination region can be extracted to the two-dimensional data area.

Third, as procedure 3 of the determination process of FIG. 1, a procedure is explained to determine that an X-ray is partly off the sample where measurement is made on luminance change in the extracted image and there is luminance change greater than a reference change (block 4). Procedure 3 has two premise conditions. The premise conditions are explained.

The first premise condition is a difference in brightness between a position to be measured and a position not to be measured. For example, where measuring a black line material, such preparation as whitening a sample placing jig. Also, where measuring an interconnect pattern on a substrate, this invention is applicable because the solder in interconnect areas is in a luminance of nearly white and other portions are green resist.

The second premise condition is that, when a sample to be measured is imaged, the sample therein is seen in a same brightness. The electronic component that automatic measurement is frequently required, in many cases, is homogeneous in material and in surface roughness. An image with an almost homogeneous brightness can be obtained.

Figure 4:
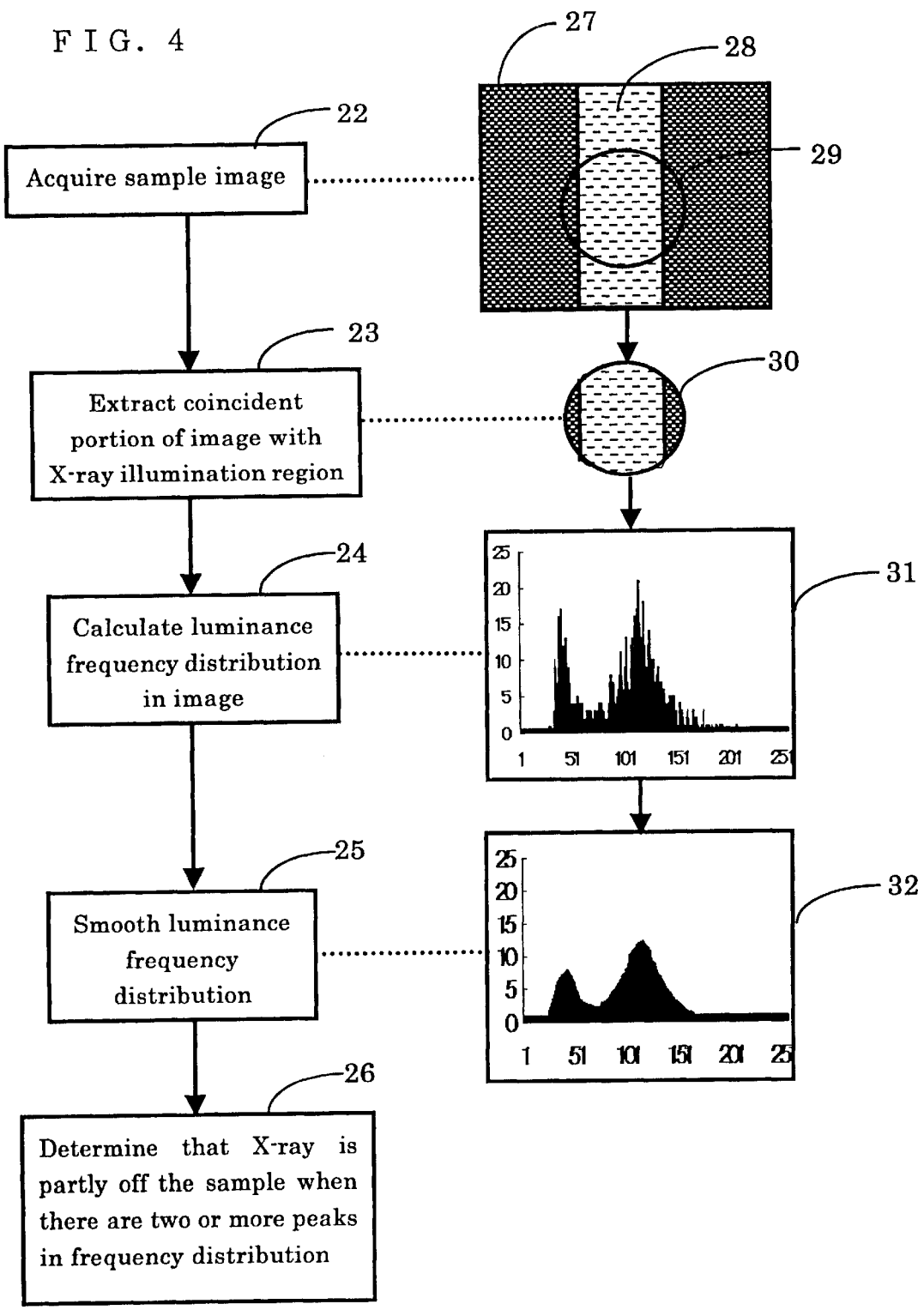
FIG. 4 is a flowchart of a procedure to determine whether an X-ray illuminated to a sample is partly off the sample or not, utilizing an image luminance frequency distribution.

The operation in the case satisfying the above two conditions is explained using FIG. 4. First, where the luminance resolution is at 256 steps, a sample 28 as a portion to be measured has a mean luminance of 115 and the mean luminance around the sample 28 is 42. An image of an X-ray illumination region 29 is extracted to obtain an image 30 of a coincident portion with the X-ray illumination region. If examining a luminance distribution in the image 30, a frequency distribution of luminance 31 is obtained. Noticing a mountain in the luminance frequency distribution, it can be read that there are two mountains in separate places. This represents that it is possible to separate the high luminance portion and a low luminance portion.

Second, explained is evenness of luminance in the portion to be measured. When viewing the two mountains in the frequency distribution of luminance 31, the degree of spread in the mountain represents deviation in luminance. Where luminance deviation is large, the two mountains overlap, making it difficult to separate between the high luminance portion and the low luminance portion. In an example of the luminance frequency distribution 31, a low luminance mountain has a standard deviation of 10.4 and the high luminance mountain a standard deviation of 19.6.

Where satisfying the two conditions, although the high luminance portion and the low luminance portion can be separated, determination is made on whether the X-ray is partially off the sample or not.

Figure 5:
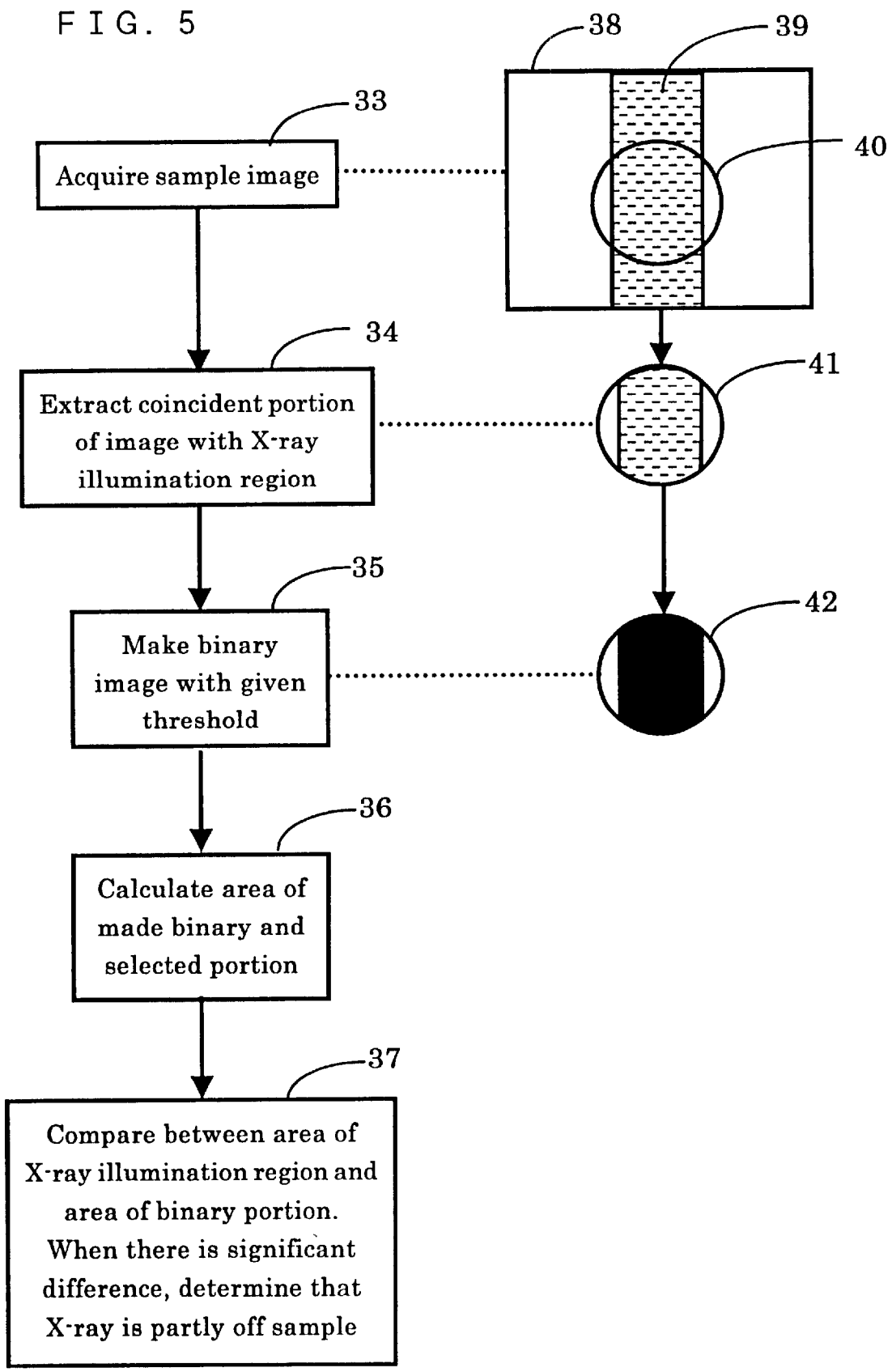
FIG. 5 is a flowchart of a procedure to determine whether an X-ray illuminated to a sample is partly off the sample or not, by making binary process on an image.

FIG. 5 is a flowchart illustrating a procedure using a binary process on an image to determine whether an X-ray illuminated to a sample is partly off the sample or not. After acquiring a sample image 38 (procedure 33), an X-ray illumination region 40 is extracted to obtain an image 41 of a portion coincident with the X-ray illumination region (procedure 34). The image 41 is then subjected to a binary process with a designated threshold to obtain a processed image 42 (procedure 35). After binarization of the image 41, an area of the X-ray illumination region and an area of a binary portion of the processed image are calculated (procedure 36). The two calculated areas are then compared, and a determination is made that the X-ray is partly off the sample when there is a significant difference between the two calculated areas (procedure 37).

Explanation is made on a fluorescent X-ray analyzing apparatus having a plurality of collimators for restricting an X-ray to be illuminated to the sample to conduct the determination process repeatedly by the number of the collimators, to select a collimator greatest in area among the collimators that X-ray is not off.

Numerals 45, 48 and 51 in FIG. 6 represent X-ray illumination regions when using collimators different in dimension. Because the X-ray illumination region 45 has a portion extended out of the sample 44, it is determined that there is an outer-extended portion by a determination process on whether or not the X-ray is partially off the sample. The X-ray illumination region 48 and the X-ray illumination region 51 are determined that there is no outside portion by the determination process on whether or not the X-ray is partially off the sample. The X-ray illumination region 48 and X-ray illumination region 51 having no outside portions are compared in area so that the apparatus finally selects the X-ray illumination region 51 greater in area. The selection of the larger X-ray illumination area helps obtain the larger fluorescent X-ray intensity per unit time and reduce statistic measurement error as small as possible.

Explanation is made on a fluorescent X-ray analysis apparatus characterized in that, in an image acquiring operation performed in process procedure 1, sample images are obtained in color, a means is provided to extract a particular color from among the obtained images and convert it into a monochromatic image, and determination can be made utilizing color information whether an X-ray illuminated to a sample is partially off the sample or not.

As an example of an image obtaining means, a color CCD camera is used to obtain an image. As an output of the CCD camera, an NTSC signal for example is outputted. The image processing section inputs the NTSC signal. As a color extraction means, for example today's image processing means can handle color images. For example, it is possible to extract a red portion from a color image. As a conversion means to monochromatic images, the luminance of an image obtained in the extraction process is read as monochromatic image luminance information, thereby enabling conversion into a monochromatic image. Utilizing this image, it can be determined that the X-ray illuminated to the sample is partly off the sample.

Explanation is made using FIG. 7 on a fluorescent X-ray analysis apparatus characterized in that, in the apparatus to perform a determination process whether an X-ray is partly off a sample or not, the information on an X-ray illumination region can be magnified independently in respective vertical direction and horizontal direction at arbitrary magnifications wherein a margin is given for a change in X-ray illumination axis deviation and change of an illumination region so that determination can be made whether an X-ray illuminated to a sample is partially off a sample or not.

Immediately after examining an X-ray illumination region and X-ray illumination position, for samples 52 and 56 in FIG. 7 a positional relationship is given by X-ray illumination regions 53 and 57. However, where the analysis apparatus has been used for a long time or where environmental change such as temperature is large, there is a possibility of deviation in X-ray illumination center position or change in X-ray illumination size. As an example thereof, explanation is made by exemplifying X-ray illumination regions 55 and 59 when deviated in illumination position. For the case on the sample 52, where a determination process is performed on whether an X-ray illuminated to the sample is partly off the sample by utilizing the X-ray illumination region 54 given a margin vertically and horizontally, determination is as partially off, enabling to avoid erroneous determination. For a sample 56 case, there is sufficiency in sample size. Accordingly, even where a determination process is performed on whether an X-ray illuminated to the sample is partly off the sample by utilizing the X-ray illumination region 58 given a margin vertically and horizontally, determination is as entirely illuminated to the sample. As for how to give a margin, experiment of changing temperature for example is conducted to inspect an amount of deviation in an X-ray illumination center position during it. Thus determining a margin from a relation to an environment of use.

As above, erroneous determination is prevented by giving a margin to an X-ray illumination region.

Explanation is made using FIG. 4 on a first concrete method that an extracted image is examined in luminance change therein to examine whether there is a luminance change higher than a reference or not.

On an image 30 in an coincident part with an X-ray illumination region, examination is made on luminance information of all the pixels. In this example, luminance information is represented in 256 steps, and a graph having a frequency on the vertical axis with luminance on the horizontal axis is given as luminance frequency distribution 31. The information of obtained frequencies is smoothed to obtain a luminance frequency distribution 32 after smoothing. The frequency distribution 31, because of having fine roughening, is filter-processed to remove high-frequency noise. In this example, mean-value filter process is conducted with a filter width of 20. The obtained information is a luminance frequency distribution 32 after smoothing. The data after smoothing is examined of peak count as an object. Where two or more peaks exist, it can be determined that the X-ray illuminated to the sample is partly off the sample.

Explanation is made using FIG. 5 on a second concrete method that an extracted image is examined in luminance change to examine whether there is a luminance change greater than a reference or not.

A binarizing process is conducted on an image 41 in a coincident part with an X-ray illumination region utilizing a given threshold, obtaining an image 42 after binarizing process. In this example, luminance information is expressed in 256 steps wherein 150 is given as a threshold in binarizing and information of extracting a dark portion is given. The image 42 after the binarizing process is examined in area of a black portion, and the black portion area is compared with the area of the X-ray illumination regions. If there is a significant difference, it can be determined that the X-ray illuminated to the sample is partly off the sample. In this example, the black portion has an area of 25000 pixels and the X-ray illumination region has an area of 29000, wherein there obviously is a significant difference. Accordingly, it can be determined that the X-ray illuminated to the sample is partly off the sample.

Explanation is made using FIG. 8 on a method on a third concrete method that an extracted image is examined in luminance change therein to examine whether there is a luminance change greater than a reference or not.

The third method is an improvement over a part of the second method wherein the information for binarization given by a human in the second method is automatically generated.

Considering an image 63 around a center of X-ray illumination, a mean luminance of around the X-ray illumination center is calculated to obtain a reference luminance. This method is applicable because there is less probability that X-ray illumination at around its center goes off the sample. In order to extract an image within a range of a given width with respect to this reference luminance as a center, calculated are a lower limit value 65 in binarization and an upper limit value 66 in binarization. Binarization is made with a portion sandwiched between the lower limit value and the upper limit value and another portion. The procedure after binarization is similar to the above-stated method wherein comparison is made between an area of an image obtained by the binarization and an area of an X-ray illumination region. Where there is a significant difference, it can be determined that the X-ray illuminated to the sample is partly off the sample.

Figure 9:
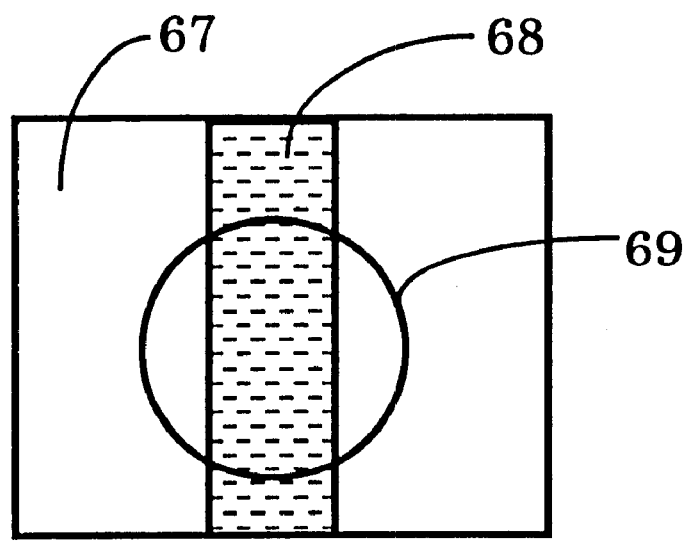
FIG. 9 is an explanatory view when conducting measurement in a state an X-ray is off an sample.

In the above two determination process utilizing a binarizing process, where determining that the X-ray illuminated to the sample is partly off the sample, the area of a sample portion obtained through measurement is taken as a sample area and the sample area is divided by the area of the X-ray illumination region to calculate a real illumination area ratio. In this state, an X-ray is illuminated to the sample. A fluorescent X-ray intensity obtained in the X-ray detection section is divided by the real illumination area ratio to thereby enable estimation on a fluorescent X-ray intensity for a case that the sample exists over an entire X-ray illumination region. Explanation is made using FIG. 9 on a fluorescent X-ray analysis apparatus characterized in that the fluorescent X-ray intensity thus estimated can be utilized in quantitative analysis.

This method is applicable for a case that a material of a part at around the sample is known and separation is possible between a fluorescent X-ray obtained from a portion around the sample and a fluorescent X-ray from the sample.

This example is in a state that a wire rod 68 having a material of an alloy of tin and lead is put on a sample stage 67 having a material of iron. Although the X-ray illumination region is in a stated extended out of the wire rod 68, in this state an X-ray is illuminated to the wire rod 68 and sample stage 67 to carry out a measurement. A range where the sample exist within the X-ray illumination region is determined by the binarizing means to obtain, for example, an area of 50pixels. Next, the X-ray illumination region 69 is measured of area by the image processing means to obtain, for example, an area of 100 pixels. As a real illumination area ratio, 50 is divided by 100 to obtain a ratio of 0.5. The intensity of an X-ray on tin and lead detected by the X-ray detector is divided by the above real illumination area ratio 0.5, thereby making possible to estimate an X-ray intensity for a case that the sample 68 exists in the entire X-ray illumination region 69. With this X-ray intensity conversion process, quantitative analysis can be carried out.

This invention can obtain five effects.

First, it can be determined whether the X-ray illuminated to a sample is partly off the sample or nor. Although conventionally the determination process has been conducted by a human, the provision of this function makes possible automatic operation without anxiety. Also, even in a a case of not in an automatic operation, where measuring such a fine region as cannot be visually determined, the apparatus can be used to make the determination. This makes operator's skill unnecessary. Also, there is an effect of good safety and sanitation, such as the operator not having to look at one point on a screen.

Second, in a case of an apparatus having a plurality of collimators to restrict an X-ray, a collimator is examined that the X-ray will not extend outside. By selecting a collimator greatest in area, it is possible to maximize an amount of the X-ray to be detected, maximizing measurement throughput. Furthermore, this operation can be executed without attendance. Where a similar operation is made in the conventional method, the similar operation cannot be performed unless all the measurement points are confirmed in shape and dimension and applicable collimator is designated for each measurement point. Automation on all of these former operations of measurement is a second effect.

Third, if in an image acquire process a color image can be once obtained and a particular color be extracted, it becomes possible to cope with a relation between such a sample as cannot be discriminated in a monochromatic image and a background. This can enlarge an application scope of the present invention.

Fourth, it is possible to give a margin for central position deviation of X-ray illumination or change in X-ray illumination size occurring where the analysis apparatus is used for a long term due to giving a margin to the dimension of an X-ray illumination region utilized in the determination process described in the first effect or where an environmental change, such as of temperature is severe. Thus, automatic operation is possible without anxiety.

Fifth, where it is determined that the X-ray illuminated to the sample is partly off the ample, an obtained X-ray intensity is converted thereby enabling utilization for quantitative analysis. In other words, a smaller sample than an X-ray illumination region can be quantitatively analyzed. The electronic component as principal one of an object to be measured has been scaled down. With a collimator possessed by the analysis apparatus, there is a case that an X-ray extends out a sample. In also such a case, the capability of performing quantitative analysis by examining an area of the object is extremely useful. It can be said that realization is possible without apparatus modification or increase of cost is a great effect for the user.

What is claimed is:

1. In a fluorescent X-ray apparatus having an X-ray generating part for illuminating an X-ray to a sample, an X-ray detecting part for detecting a fluorescent X-ray from the sample, a collimator part for restricting the X-ray illuminated to the sample, an imaging part for imaging a sample image, and an image processing part for image-processing an imaged image, a fluorescent X-ray analysis method comprising the steps of:

previously examining as a former process a positional relationship between a sample image to be acquired in the imaging part and an illumination region of an X-ray;

acquiring as process procedure 1 an image of the sample as a monochromatic image;

extracting as process procedure 2, in the acquired image of the sample, a coincident portion of the image with the X-ray illumination region by the image processing part; and examining as process procedure 3 a luminance change in the extracted image and, where there is a luminance change greater than a reference, determining whether or not the X-ray illuminated to the sample is partly off the sample.

2. A fluorescent X-ray analysis method according to claim 1, wherein the collimator part is provided with a plurality of collimators to restrict the X-ray illuminated to the sample, and including the steps of repeatedly executing a determination process using different ones of the collimators, and selecting a collimator having the greatest X-ray illumination area from among the collimators whose X-ray illumination area is not off the sample.

3. A fluorescent X-ray analysis method according to claim 1 or claim 2, wherein the process procedure 1 acquires the image of the sample as a color image, extracts a particular color from the acquired image, and converts same into a monochromatic image.

4. A fluorescent X-ray analysis method according to claim 1, wherein in the process procedure 2, information of the X-ray illumination region is magnified at arbitrary magnifications independently in a vertical direction and a horizontal direction to provide a margin for axis deviation of X-ray illumination and change in illumination region.

5. A fluorescent X-ray analysis method according to claim 1, wherein the process procedure 3 calculates a frequency distribution of luminance in the extracted image, performs a smoothing processing on frequency distribution data, examines the number of peaks concerning luminance from a frequency distribution after smoothing, and determines that the X-ray illuminated to the sample is partly off the sample where two or more peaks are found.

6. A fluorescent X-ray analysis method according to claim 1, wherein the process procedure 3 binarizes the extracted image with a designated threshold, measures an area of pixels of a designated value of 1 or 0 after binarization, and determines that the X-ray illuminated to the sample is partly off the sample where there is a significant difference between an area of an X-ray illumination range and an area measured.

7. A fluorescent X-ray analysis method according to claim 1, wherein the process procedure 3 renders an image luminance in the vicinity of the center of the X-ray illumination region as a reference luminance, measures in the extracted image an area of pixels close to the reference luminance, and determines that the X-ray illuminated to the sample is off the sample where there is partly a significant difference between an area of an X-ray illumination range and an area measured.

8. A fluorescent X-ray analysis method according to claim 7, wherein when the process procedure 3 determines that the X-ray illuminated to the sample is partly off the sample, rendering an area of a sample portion obtained by measurement as a sample area, dividing the sample area by the area of the X-ray illumination region to calculate a real illumination area ratio, illuminating an X-ray in this state, dividing a fluorescent X-ray intensity obtained in the X-ray detection part by the real illumination area ratio thereby enabling estimation of a fluorescent X-ray intensity where the sample exists in the entire X-ray illumination region, and utilizing the estimated fluorescent X-ray intensity for quantitative analysis.

* * * * *